United States Patent
Hossack et al.

(10) Patent No.: US 7,837,624 B1
(45) Date of Patent: Nov. 23, 2010

(54) MEDICAL DIAGNOSTIC ULTRASOUND IMAGING METHODS FOR EXTENDED FIELD OF VIEW

(75) Inventors: John A. Hossack, Palo Alto, CA (US); Linyong Pang, Stanford, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 09/196,986

(22) Filed: Nov. 20, 1998

(51) Int. Cl.
*A61B 8/00* (2006.01)
*G06K 9/32* (2006.01)

(52) U.S. Cl. .................. 600/443; 600/437; 382/294

(58) Field of Classification Search .......... 600/437, 600/443, 444, 447, 454–456, 448, 466–467; 128/916; 382/128, 131, 293–296
See application file for complete search history.

(56) References Cited

U.S. PATENT DOCUMENTS

| | | | |
|---|---|---|---|
| 5,229,933 A | 7/1993 | Larson, III | |
| 5,474,073 A | 12/1995 | Schwartz et al. | |
| 5,479,926 A | 1/1996 | Ustuner | |
| 5,538,004 A * | 7/1996 | Bamber | 600/443 |
| 5,566,674 A | 10/1996 | Weng | |
| 5,575,286 A * | 11/1996 | Weng et al. | 600/444 |
| 5,613,013 A * | 3/1997 | Schuette | 382/124 |
| 5,655,535 A * | 8/1997 | Friemel et al. | 600/443 |
| 5,771,895 A * | 6/1998 | Slager | 600/462 |
| 5,782,766 A * | 7/1998 | Weng et al. | 600/443 |
| 5,831,168 A * | 11/1998 | Shinomura et al. | 600/437 |
| 5,846,200 A * | 12/1998 | Schwartz | 600/443 |
| 5,873,830 A | 2/1999 | Hossack et al. | |
| 5,899,861 A | 5/1999 | Friemel et al. | |
| 5,910,114 A * | 6/1999 | Nock et al. | 600/437 |
| 5,946,425 A * | 8/1999 | Bove et al. | 382/294 |
| 5,956,418 A * | 9/1999 | Aiger et al. | 382/294 |
| 6,014,473 A * | 1/2000 | Hossack et al. | 382/294 |
| 6,117,081 A | 9/2000 | Jago et al. | |
| 6,126,598 A | 10/2000 | Entrekin et al. | |
| 6,128,108 A | 10/2000 | Teo | |
| 6,152,878 A | 11/2000 | Nachtomy et al. | |
| 6,162,174 A | 12/2000 | Friemel | |
| 6,210,328 B1 | 4/2001 | Robinson et al. | |
| 6,224,552 B1 | 5/2001 | Jago et al. | |

OTHER PUBLICATIONS

Hoskins, P.R. et at "Scan-plane Vector Maps and Secondary Flow Motions in Arteries", European Jrnl of Ultrasound Vol. 1, 1994, pp. 159-169.*

Entrekin, R et al., "Real Time Spatial Compounding Imaging in breast ultrasound: technology and early clinical experience", Medica Mundi, vol. 43, Issue 3, Sep. 1999, pp. 35-43.*

Blinn, James F., *Compositing, Part I: Theory*, IEEE Computer Graphics and Applications, Sep. 1994, vol. 14, No. 5, pp. 83-87.

Office Action issued by German Patent and Trademark Office dated Mar. 29, 2010 in German counterpart application No. 101 41 516.8-35.

* cited by examiner

*Primary Examiner*—Eric F Winakur (57) ABSTRACT

A medical diagnostic ultrasound imaging system aligns substantially co-planar two-dimensional images to form an extended field of view using improved methods that speed the alignment, use Doppler processors to alert the user when transducer motion relative to the imaged region is excessive, and provide a longitudinal sectional view of a blood vessel and surrounding tissue.

31 Claims, 8 Drawing Sheets

Fig. 2

$(\Delta X, \Delta Z, \Delta \Theta)$

| | O | PIXEL ROTATION | PIXEL INDEX. | MOTION |
|---|---|---|---|---|
| | | | 1 | 0 |
| | | | 2 | 0 |
| | | | 3 | 0 |
| | | | 4 | 0 |
| | | | 5 | 0 |
| | | | 6 | 0 |
| | | | 7 | 0 |
| | | | 8 | 0 |
| | | | 9 | 0 |
| | | | 10 | 0 |

Fig. 7

1 PIXEL ROTATION

| PIXEL INDEX | MOTION |
|---|---|
| 1 | +1 |
| 2 | +1 |
| 3 | +1 |
| 4 | 0 |
| 5 | 0 |
| 6 | 0 |
| 7 | 0 |
| 8 | -1 |
| 9 | -1 |
| 10 | -1 |

Fig. 8

2 PIXEL ROTATION

| PIXEL INDEX | MOTION |
|---|---|
| 1 | +2 |
| 2 | +2 |
| 3 | +1 |
| 4 | +1 |
| 5 | 0 |
| 6 | 0 |
| 7 | -1 |
| 8 | -1 |
| 9 | -2 |
| 10 | -2 |

MEDICAL DIAGNOSTIC ULTRASOUND IMAGING METHODS FOR EXTENDED FIELD OF VIEW

The present patent document claims the benefit of the filing date under 35 U.S.C. § 119(e) of Provisional U.S. Patent Application Ser. No. 60/105,703, filed Oct. 26, 1998, which is hereby incorporated by reference.

BACKGROUND

The present invention relates to medical diagnostic ultrasonic imaging, and in particular to improved methods used in connection with the alignment of two or more partially or entirely overlapping images.

U.S. Pat. No. 6,014,473, filed Aug. 22, 1997, assigned to the assignee of the present invention and hereby incorporated by reference in its entirety, describes systems for acquiring, aligning and registering multiple medical diagnostic ultrasound images. Such alignment is used both to determine the motion between two selected images as well as to provide the information needed to composite an extended image from two or more selected ultrasound images. That is, two coplanar tracking images can be aligned and in this way the relative motion of the transducer between the times of the two tracking images can be obtained. Similarly, two or more substantially coplanar diagnostic images can be aligned and then composited to form an extended field of view.

The alignment method described in U.S. Pat. No. 6,014,473 aligns two images in translation and rotation as follows. An array of rotation axes is defined. For each of these axes a test block from the respective parent image is rotated about it by a few angular steps (e.g. −4 to +4 degrees). For each rotation, the test block is then translated in each of X and Y until an optimal match is found using the minimum sum of absolute differences (MSAD) technique. The search is thus:

```
For each test axis location, loop over:
    For each rotation amount, loop over:
        For each translation in X, loop over:
            For each translation in Y,
                Calculate SAD,
                Is SAD<MSAD?
                    Y: Update MSAD and continue search
                    N: Continue search
```

This alignment method is effective, but in some applications it requires substantial calculation time to find the best alignment.

The present invention is directed in part to an improved alignment method that is particularly efficient and quick to execute.

SUMMARY

The alignment method described in the following detailed description operates with at least first and second medical ultrasonic diagnostic images. As a first step in the alignment method, a test block from the first image is matched in translation only with a corresponding test block of the second image. Once the matching translation is found for the test blocks, then a matching rotation is found for the test blocks of the first and second images, given the previously determined translation.

By first matching the test blocks in translation and then in rotation, a particularly efficient, high-speed method is provided for determining registration information for the respective images.

The scope of this invention is defined by the following claims, and nothing in this introductory section should be taken as a limitation on those claims.

DETAILED DESCRIPTION OF THE PREFERRED EMBODIMENTS

Figure 1:
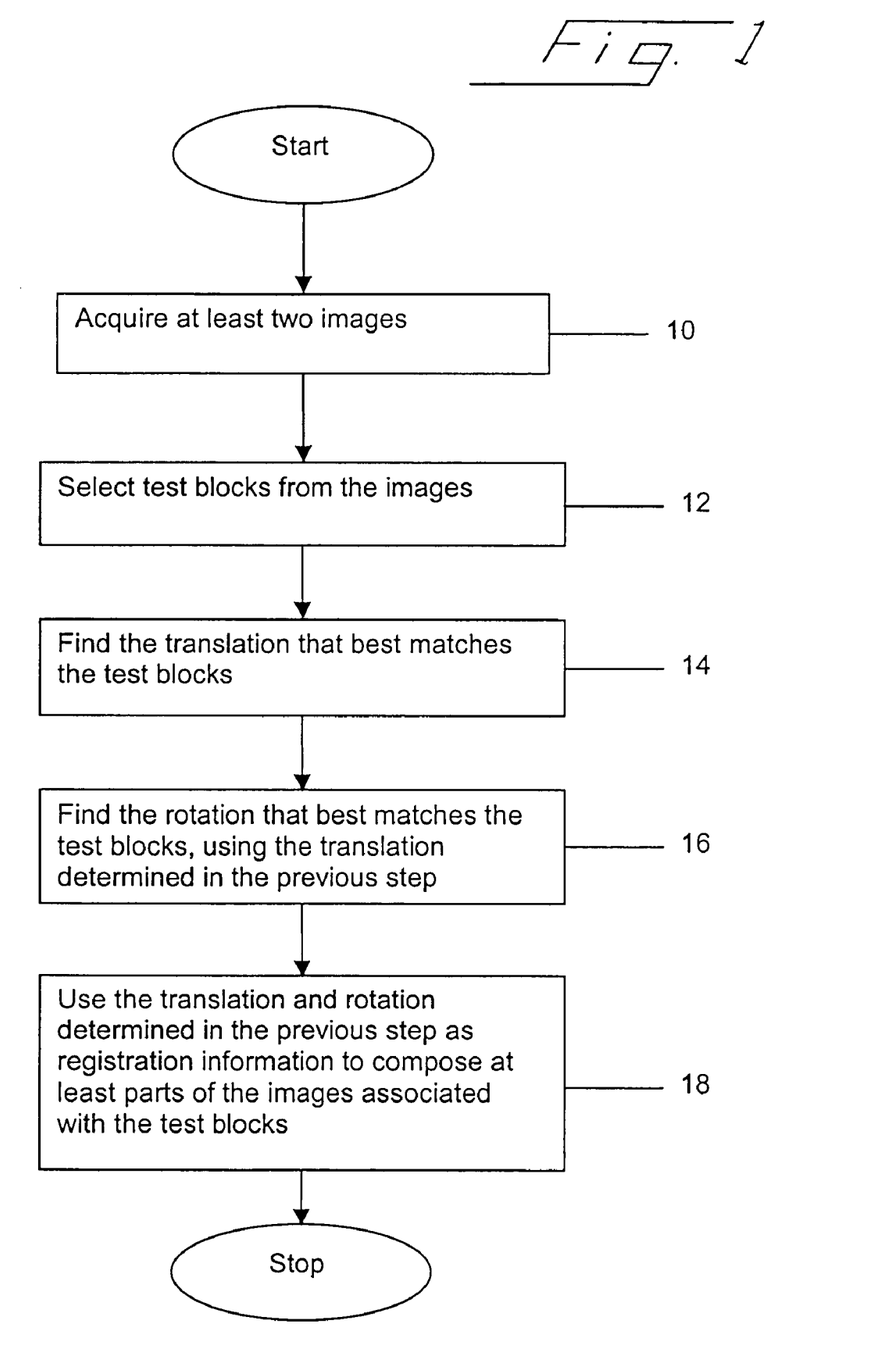
FIG. 1 is a flow chart of a method that incorporates a presently preferred embodiment of this invention.

Turning now to the drawings, FIG. 1 shows a block diagram of one implementation of the method of this invention. In a first step 10 at least two medical diagnostic ultrasound images are acquired, using any suitable technology. For example, the Sequoia or Aspen systems of Acuson Corporation can be used to acquire these two images in any suitable manner. As discussed in greater detail below, these images may be in any desired imaging mode, including B-mode, Color Doppler mode, and fundamental mode or harmonic mode (including harmonic imaging of contrast agent and harmonic imaging of tissue without added contrast agent). On occasion, these originally acquired images will be referred to in this specification as parent images.

The two images are preferably substantially coplanar and partially overlapping, and can be obtained as separate frames acquired as a transducer probe is translated and potentially rotated in the XZ plane. The widest variety of transducer probes can be used, including conventional external probes as well as intracavity probes, such as transducer probes designed for insertion into the esophagus or other body cavities, intravascular and other catheter-based transducer probes, and intraoperative transducer probes (transducer probes designed for use during surgical operations in direct contact with internal organs).

Figure 2:
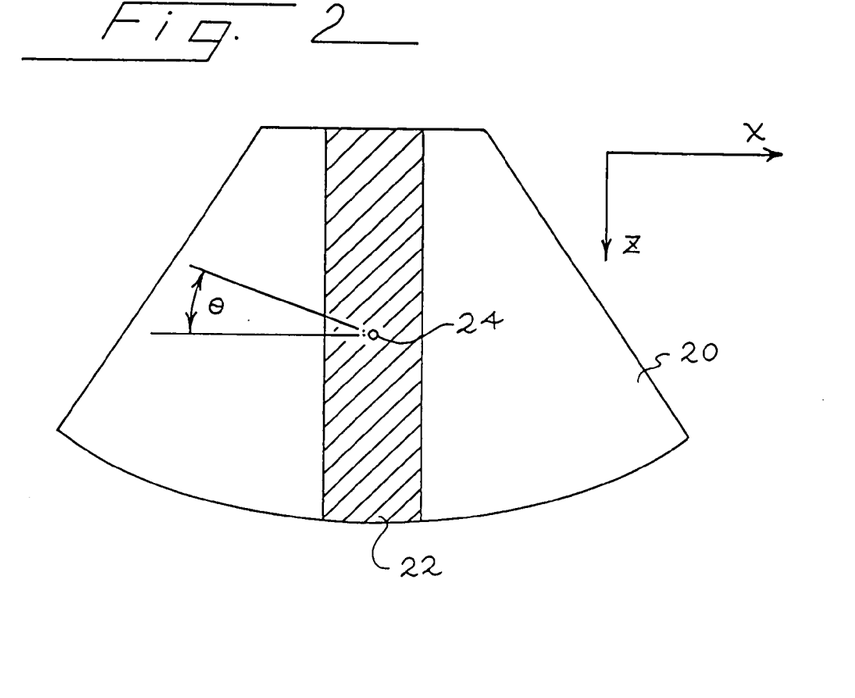
FIG. 2 is a schematic diagram of a parent image and a test block suitable for use in the method of FIG. 1.

In step 12, test blocks are selected from the images acquired in step 10. FIG. 2 shows one example, in which a test block 22 is shown as a central strip taken from a parent image 20. As described below, the test block 22 can be shaped as desired, and various techniques can be used to modify the test block as compared to the parent image. For example, the test block can be reduced in complexity by various filtering, decimation, and other techniques as described below. FIG. 2 shows the conventional X (azimuthal) and Z (range) dimensions as they relate to the parent image and the test block 22.

Returning to FIG. 1, the next step 14 is to find the translation in the XZ plane that matches the test blocks from the two images. As explained below, the match can be measured in many ways, including the minimum sum of absolute differences (MSAD) technique and various correlation techniques that utilize multiplications. Note that in step 14 the test blocks are merely translated with respect to one another and are not rotated. As described below, the location, range, and orientation of the translations that are used in step 14 can be selected adaptively to minimize the search time.

In step 16, the test blocks are aligned in translation using the matching translation of the preceding step and then rotated about a central axis 24 (FIG. 2) to find the angle of rotation that best matches the test blocks. As before, the angles of rotation that are searched can be selected adaptively based on previous searches to speed the search.

In the method of FIG. 1, the matching translation and rotation angle are found independently. This offers an advantage over a method that detects multiple translations from among several blocks and infers the rotation subsequently. In practice, motion may be irregular in either, or both, translation and rotation in a completely independent fashion. Typically, translation errors are of lesser consequence since they result in less serious cumulative geometric errors. Angular errors can have a more serious impact since the errors tend to accumulate and an angular error results in increasing translational errors in subsequently acquired frames. Therefore, it is preferable to independently control the search range for valid angular motions between frames.

Figure 3:
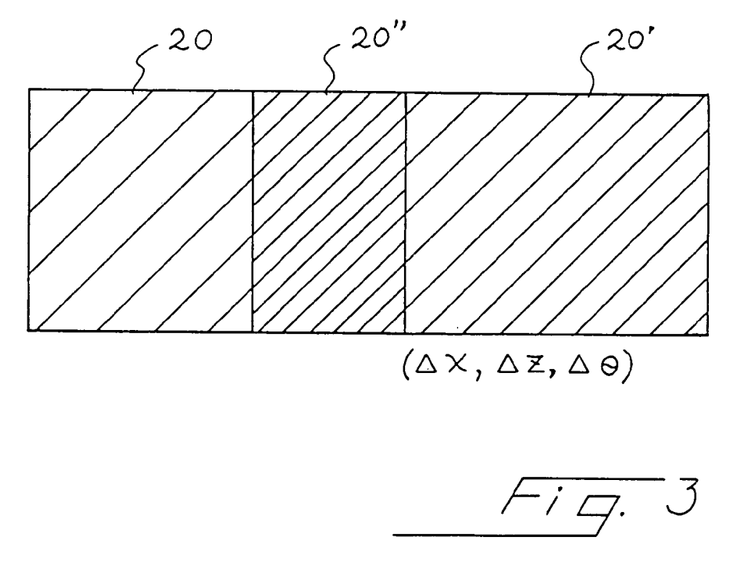
FIG. 3 is a schematic diagram of an extended field of view generated by the method of FIG. 1.

Finally, in step 18 the matching translation and rotation from the previous steps are used as registration information to composite at least parts of the original parent images. FIG. 3 shows one example in which two parent images 20, 20' are composited with one another. The parent images 20, 20' overlap in an overlapping region 20", and the registration information ($\Delta X$, $\Delta Z$, $\Delta \theta$) is used to align the parent images 20, 20'.

The method of FIG. 1 preferably takes advantage of the nature of real motion of a transducer over the tissue. Typically, translation along the X (azimuth) axis is far greater than translation along the Z (range) axis; the transducer slides along the surface and is not pressed into the tissue. Rotation effects are generally relatively modest compared to translation effects. This will certainly be true for the most common applications—such as scanning the abdominal surface or scanning along necks or legs.

The test block shape is preferably optimized to facilitate rotation determination. The block is made narrow in the azimuthal direction (e.g. 32 pixels along the X axis) and long in the range direction (e.g. 320 pixels—or almost the entire available image depth along the Z axis). The reason for this is that as the block is rotated by small amounts, the effect of rotation can be approximated by translating rows of pixels in the top and bottom regions of the test block. If the pixel block were square, one would have to translate the pixels in both X and Z, since the motion in the Z direction would be non-negligible.

Figure 4:
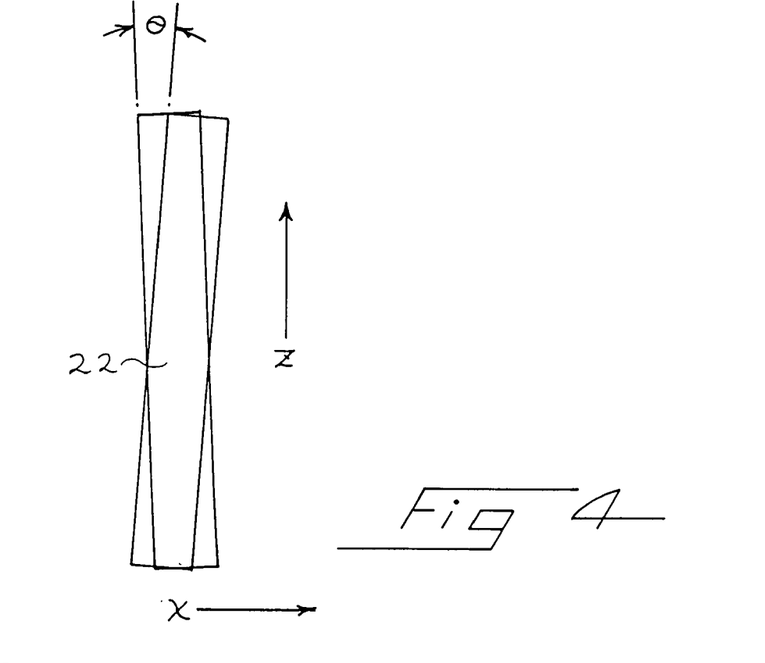
FIGS. 4 and 5 are diagrammatic views of two different test blocks suitable for use in the method of FIG. 1.
Figure 5:
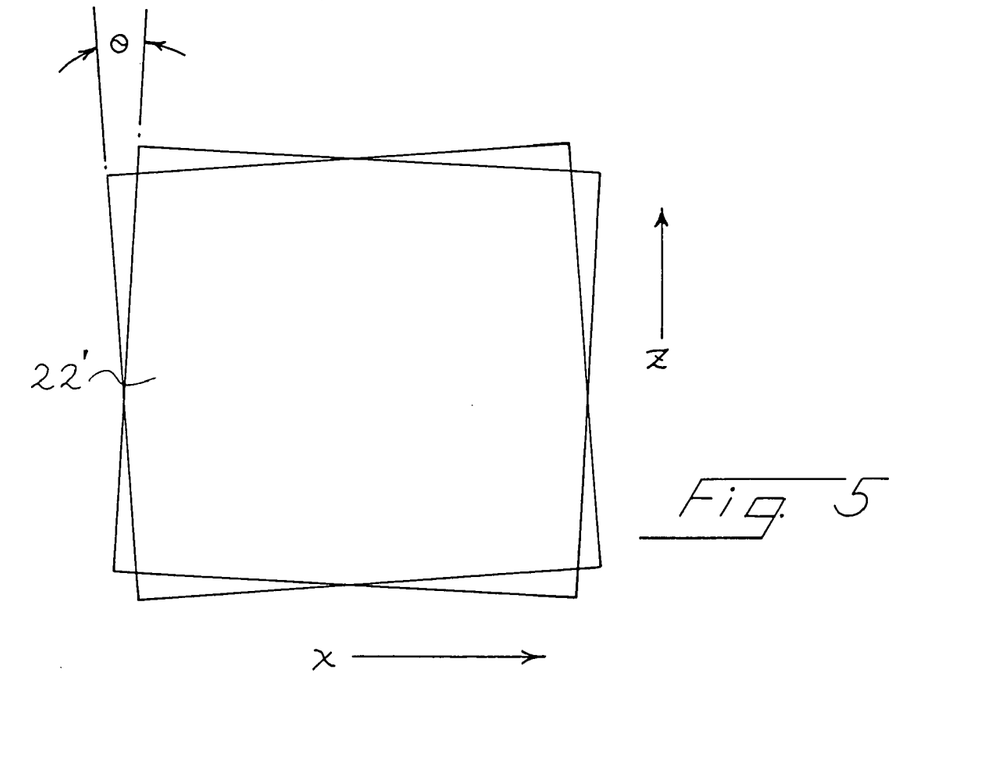

FIGS. 4 and 5 illustrate this effect. In FIG. 4 the test block 22 is rotated by an angle $\theta$. To first order, the motion of each row of pixels along the X axis is simply translation along the X axis, and none of the pixels of the test block 22 moves substantially in the Z direction. In contrast, when a wider test block 22' is used as shown in FIG. 5, a comparable rotation through the angle $\theta$ produces substantial motion along the Z axis for pixels near the corners of the test block 22'. For this reason, the ratio of the range extent to the azimuthal extent of the test block is preferably greater than 5, more preferably greater than 9, and in the embodiments described below substantially equal to 10.

The search of step 14 is typically primarily in the azimuthal direction, but the search can also contain a small search (a few pixels) in the range direction. The search is preferably conducted firstly in the azimuthal direction only, followed by a fine scale, two-dimensional search in both X and Z.

The search of step 16 is most efficiently performed by generating a pixel offset table for each angular search, since high accuracy and high speed are both important. Also, small rotations are far more likely than large rotations. Therefore the rotations are typically in terms of single pixel motion increments at the extremes (top and bottom) of the test block.

Preferably, a pixel offset table is generated once when the program is started. A predefined angular search range is defined, e.g. −5 to +5 degrees in 0.2 degree steps. For every angular step one increments down the pixel block in the range direction and calculates the associated azimuthal (X) direction offset for the particular angle and pixel location in the range direction. The pixel offset is defined by the following equation:

$$\text{Round}((pixel\_index * \tan(theta)),$$

where Round is a function returning the nearest whole number, pixel_index is the index of the pixel in the range direction with respect to the center of the text block (i.e. the axis of rotation), and theta is the particular angle. In this example, pixels are assumed to be square. If the pixels are not square, the above equation is modified to correct for the pixel aspect ratio, as for example as follows:

$$\text{Round}\left(\left(\frac{pixelwidth}{pixelheight}\right) pixel\_index * \tan(theta)\right).$$

Consider as an example, an image which extends over 301 pixels in the range direction. The center pixel in the range direction is 151. Consider a pixel 10 pixels down in the range direction and a selected angle equal to +0.5 degrees. The pixel offset entry for this pixel depth and selected angle is:

$$\text{Round }((151-10)*\tan(0.5*pi/180)=\text{Round }(1.23)=1$$

This process is repeated for all pixel depths and rotation angles to fill the pixel offset table, and the process is performed only once per program run.

Figure 6:
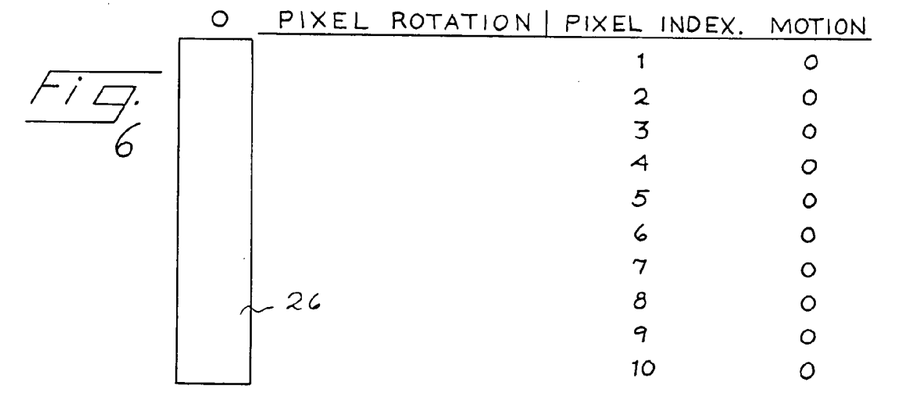
FIGS. 6–8 are diagrammatic views of test blocks rotated by 0, 1 and 2 pixels, respectively.
Figure 7:
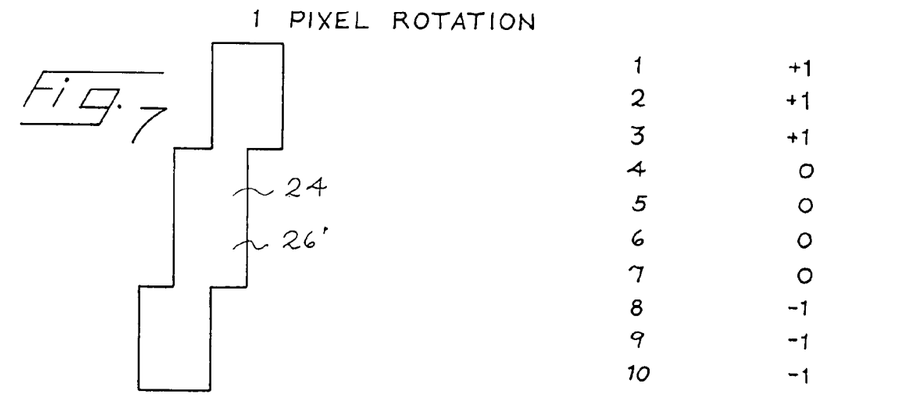
Figure 8:
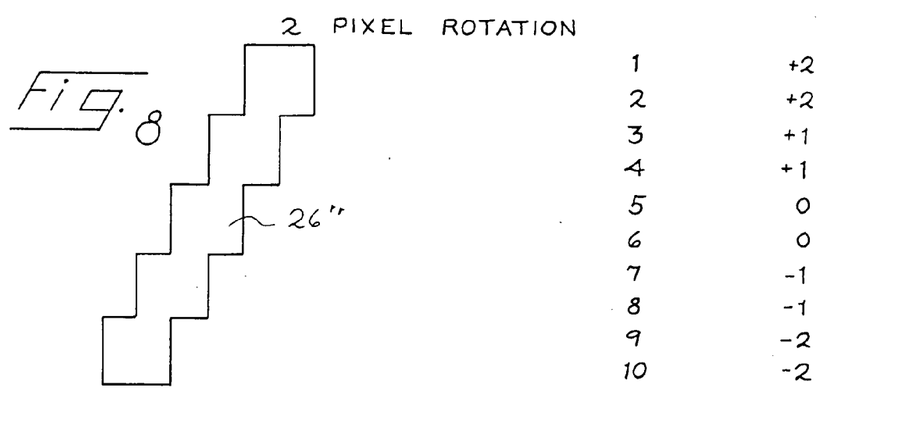

FIGS. 6, 7 and 8 illustrate three such pixel offset tables in simplified form. FIG. 6 shows a ten-pixel offset table appropriate for zero rotation. As shown at 26, the rotated test block is identical to the original test block. FIG. 7 shows an offset table for a rotation of one pixel in a clockwise direction about the axis 24. The motion ranges from +1 pixel to −1 pixel over the pixels 1 through 10, and the rotated test block is shown at 26'. FIG. 8 shows an offset table appropriate for rotation of 2 pixels in a clockwise direction, and the motion plotted in the table ranges from ±2. The rotated test block 26" shows the manner in which pixels are translated along the X direction, without translation along the Z direction. Similar tables can be created for anti-clockwise rotations.

For both steps 14 and 16 of FIG. 1, it is beneficial to calculate the motion to sub-step-size accuracy for both translation and rotation. This can be done by fitting a quadratic to the values around the MSAD minimum. Having found the equation for the fitting quadratic, the true minimum to sub-step-size accuracy is determined from the zero in the quadratic equation after differentiating. In this specification step size corresponds to the pixel search resolution for translation and the angular step resolution for rotation.

Once the matching translation and rotation are determined, the motions of all points along the central axis of the sub-block are known. If one considers the rotation as an indication of slope and the translation as a constant, we have the essential components for defining motion in terms of y=mx +c where c is the translation amount, m is the slope or tan (angle of rotation), and in this case x is the range component and y is the translation amount at that range along the X or azimuthal axis. In this way, the motions of all points on the plane may be found in order to move one image into registration with another.

The extended field of view processing described above can be performed immediately after image acquisition and displayed on the ultrasound display of the acquisition system. Alternately, such extended field of view processing can be performed after the fact on a remote computer using stored image data.

Further details regarding preferred implementations of the method described above and related methods are set out below.

Figure 9A:
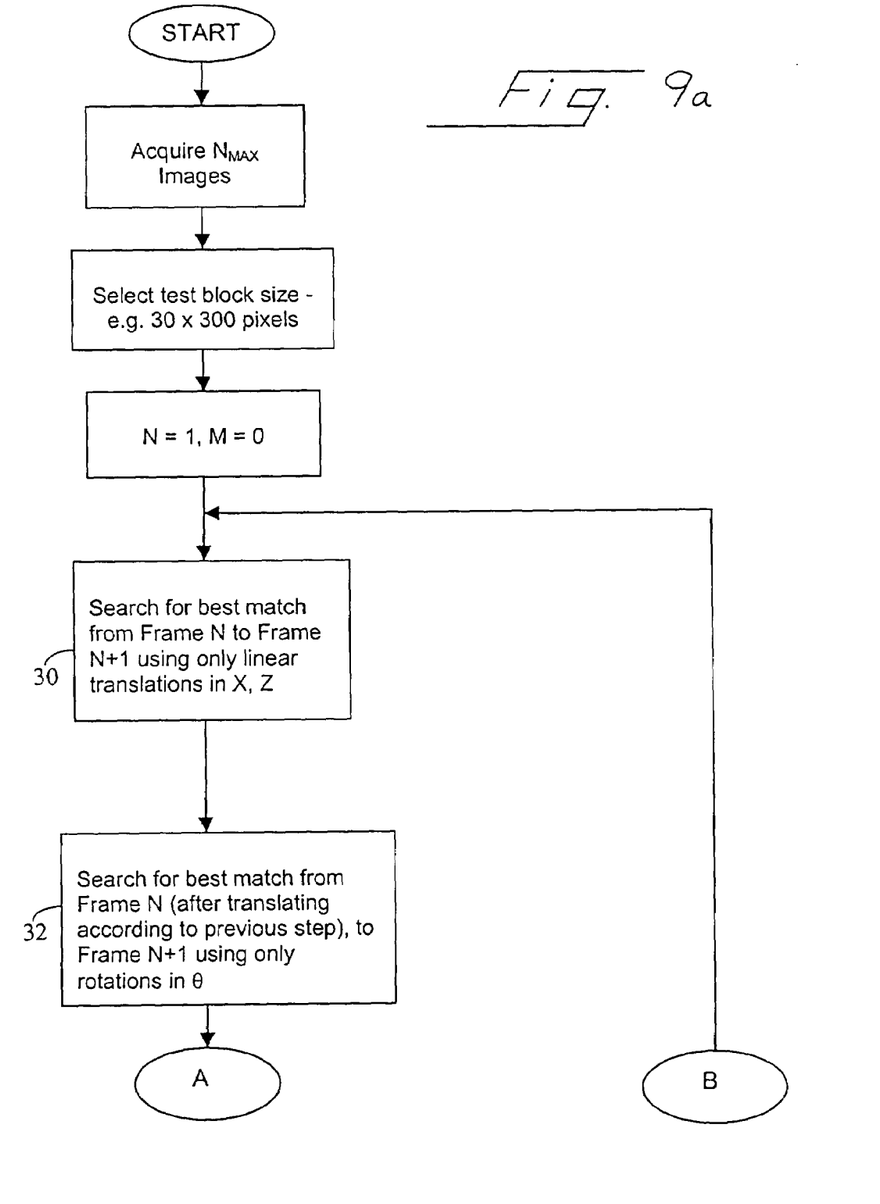
FIGS. 9a and 9b combine to form a flow chart of another preferred embodiment of the method of this invention.
Figure 9B:
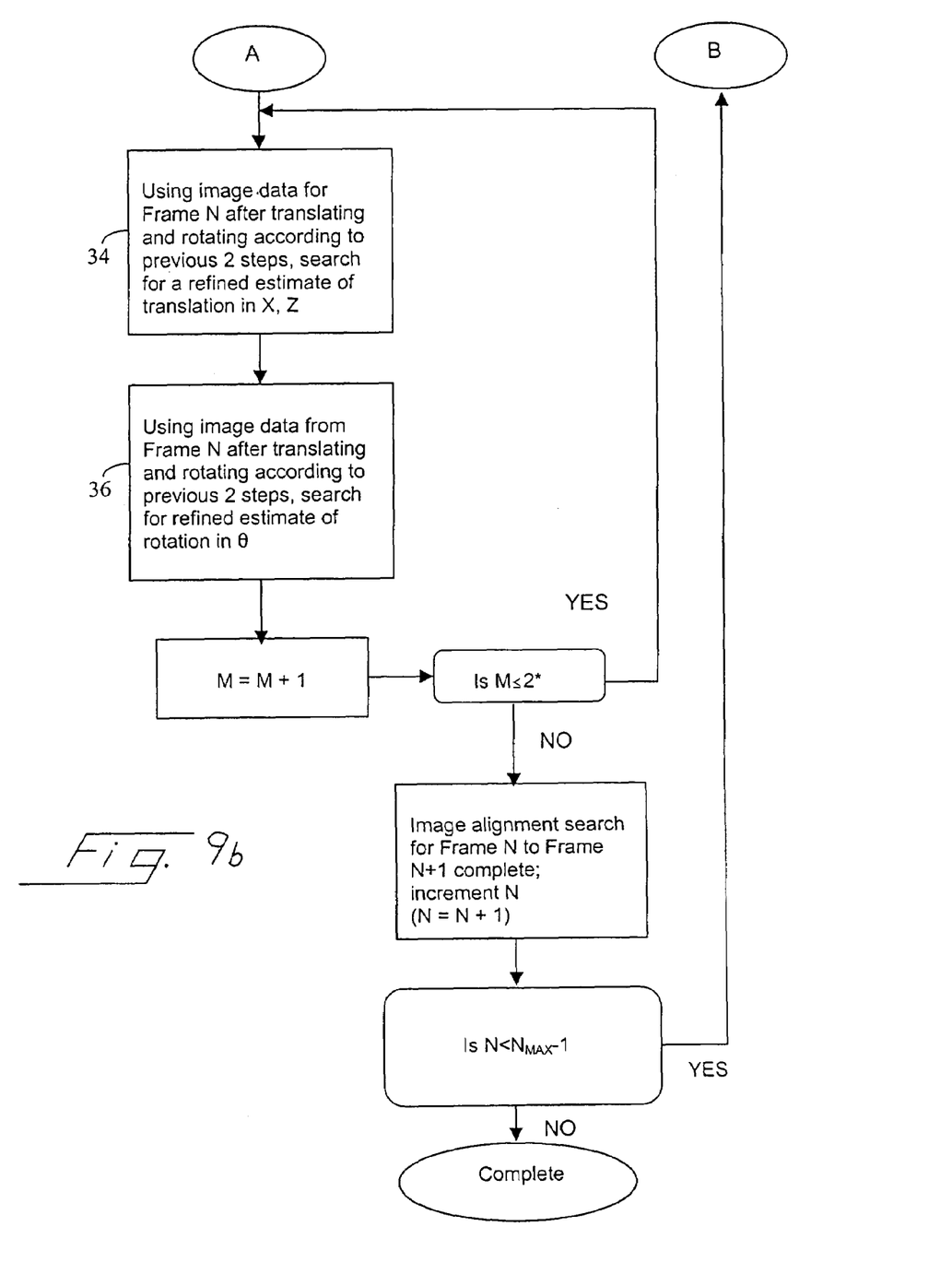

1. An iterative search can be used as set out below and as shown in FIG. 9.

Process:
(a) In step 30, search first for a match in terms of translation (either X only or X and Z).
(b) In step 32, search for match in terms of rotation, taking account of the translation found in step (a).
(c) Taking account of the match from steps 30 and 32, determine in step 34 if a translation (X and/or Z) can be found that provides a better match.
(d) Taking account of the match for translation and rotation obtained from steps 30, 32 and 34, search in step 36 for a rotation that provides a better match.
(e) Repeat steps 34 and 36 using updated estimates of translation and rotation.

It steps 30, 32, 34 and 36, it is preferred to find a best match in each case. Alternately, in each of these steps a high speed search can be used that provides a better match, though the search is too fast or approximate to find the best match. As used herein, the term "match" is intended broadly to encompass best matches as well as improved matches.

The number of times steps 34 and 36 are repeated can be determined in various ways. In the illustrated embodiment, M (the number of times steps 34 and 36 have been executed) is compared with a constant, equal to 2 in this embodiment. The constant can be greater if desired. Alternately, steps 34 and 36 can be repeated until a measure of the quality of the match (such as the ratio of the minimum SAD to the mean SAD) reaches some predetermined acceptable level, or alternately until a larger number of repetitions has been completed.

By way of example, the test block width may be set to 16×N, where N is a small integer. For N=2, this results in a width in the azimuthal direction of 32. The first translation matching step 30 of the iterative method of FIG. 9 can be in the X direction only, e.g. over a range of ±32 pixels. The search region may be varied adaptively based on previous estimates of motion in the X direction, and the range may be made less than ±32 pixels. The first rotation matching step 32 of the iterative method of FIG. 3 can be over a range of ±3 degrees. The second translation matching step 34 can be over a range of ±2 pixels in the X direction and ±1 pixels in the Z direction. The second rotation matching step 36 can be over a range of ±0.5 degrees.

2. The test block need not be tall and narrow, but as described above, such a shape for the test block provides advantages.

Consider a rectangular test block 30 pixels wide and 300 pixels high. Assume individual pixels are square. For this test block, for rotations up to 2.42 degrees there is no requirement for any pixel to shift in the Z direction by more than 0.5 pixels. Therefore, for rotations up to 2.42 degrees Z motion calculations can be ignored. Being able to ignore Z motion calculations has two advantages:

(a) Z motion calculations are not required; this saves computation time.
(b) Pixel rows in the reference frame (old frame) and the test position frame (new frame) both occupy consecutive memory locations (assuming pixels are ordered along rows in memory, that is, as a 2D array is read, pixel address first increments in X, followed by increments in Y after each row has been read). This ordering makes the programming simpler and faster. In particular it greatly facilitates the use of pointer-based programming and also makes the manipulations of blocks of pixels in parallel fashion far more tractable. For example, using Intel Pentium™ microprocessors with MMX™, this approach allows for manipulation of eight 8-bit binary numbers in parallel. The fact that pixels are grouped continuously in rows in both the old and the new frames facilitates easier implementation.

In contrast, if the pixel block is 300 pixels wide by 300 pixels high, then rotations of more than 0.19 degrees result in Z motions of more than 0.5 pixels in at least some pixels. Experience indicates that rotational motions between successive frames are frequently greater than 0.19 degrees but rarely greater than 2.42 degrees. In cases where Z motion is greater than 0.5 pixels, then it is still quite possible to reassign pixels from the Z shifted locations to the new frame pixel block so that an accurate rotation motion calculation can be performed.

3. Color Doppler ultrasound image data (Velocity, Energy or combinations) may form part or all of the images used with this method. If both B-mode data and Color data are available for display, then the B-mode data for the entire pixel block can be used to determine image registration information, and the motion calculated for a particular B-mode region can also be applied to the related (superimposed) Color region.

4. Fundamental or harmonic data may form part or all of the images used with this method.

5. Image data can be pre-processed prior to motion estimation and post-processed after composition (image registration). Examples include the following:

(a) Gray scale remapping, i.e. the as-acquired 0–255 range of gray scale values is remapped using a non straight line function.
(b) As an example of the above, contrast enhancement (e.g. histogram equalization) is used. As another example, 24 bit RGB data is decimated to 8 bit gray data.
(c) Pixel contrast resolution is decimated to speed up motion estimation, e.g. 0–255 pixel levels are mapped to 0–15, or even to 0–1 (i.e. only two binary levels) prior to motion estimation.
(d) Image brightness is altered. The resultant image is passed through a 0–255 mapping function that increases the mean pixel level (but clips the upper end at 255 to prevent wrapping beyond 255 and back to low integer numbers (associated with near black)).
(e) Image data is filtered in some way (e.g. low-pass filtered).

(f) The output image is speckle reduced (e.g. low-pass filtered).

6. The preferred motion merit function is typically MSAD (Minimum Sum of Absolute Differences); however, other matching techniques, such as finding the matching translation/rotation using cross-correlation (sum of multiplies) techniques may also be used.

7. Sub-pixel estimation can be applied to translation, and sub-angular-step-size estimation can be applied to rotation calculations.

As an example, the levels of the sum of absolute differences (SAD) for the minimum and its neighbors are compared to determine the likely position of the minimum to sub-pixel resolution. A simple way to do this is to fit a quadratic equation ($y=ax^2+bx+c$) to three points (the pixel y2 with the minimum SAD plus the next-neighboring pixels y1 and y3 on each side). The x values for these three data points are x1, x2 and x3, and these x values are typically separated by unity (the pixel spacing for translation searches and the angular step size for rotation searches). Data for three points (x1, y1), (x2, y2), x3, y3) are solved simultaneously for the equation $y=ax^2+bx+c$. In this way a, b and c (c not strictly needed) are found. The derived quadratic equation is differentiated and set equal to zero to solve for:

$$2ax+b=0.$$

In this way, the value of x to sub-step-size resolution is found.

8. The pixel data used in the test block may be pre-scan-conversion acoustic line data or post-scan-conversion video data. The pixel data for the test block can be envelope detected, raw RF, baseband quadrature (I,Q), ideally processed to give coherency between adjacent lines as described in Wright U.S. Pat. No. 5,623,928, assigned to the assignee of the present invention.

9. The images used to create the test blocks may be acquired at the rate of one receive line per transmit line or at the rate of multiple receive lines per transmit line as described in Wright U.S. Pat. No. 5,685,308, assigned to the assignee of the present invention.

10. As described in U.S. Pat. No. 6,014,473 poor estimates of motion can be identified. A poor estimate of motion may be determined based on a comparison of the level of the MSAD compared with the mean SAD. Also, a poor estimate of motion is often associated with a dissimilarity between the present estimate and previous estimates. As described in U.S. patent application Ser. No. 08/916,585, these various available confidence factors can be combined (e.g. using fuzzy logic) or used independently (e.g. if a given MSAD is unacceptable, a previous frame-to-frame motion estimate can be used).

As one example, the MSAD can be compared with a threshold to determine if the corresponding estimate of motion is reliable. One suitable threshold is equal to the number of pixels in the test block multiplied by a constant, such as 5 for example. In the event the MSAD for a particular estimate of motion is less than the threshold and is therefore indicative of a reliable estimate of motion, then the calculated estimates of motion (i.e. $\Delta X$, $\Delta Z$, and $\Delta \theta$) are used and three variables are updated as follows:

$$history\_\Delta X = (history\_\Delta X + 3*\Delta X)/4,$$

$$history\_\Delta Z = (history\_\Delta Z + 3*\Delta Z)/4,$$

$$history\_\Delta \theta = (history\_\Delta \theta + 3*\Delta \theta)/4.$$

The weights used in the weighted averages of the foregoing equations are merely examples of possible choices. Other alternatives can be used. In the event the MSAD associated with a particular estimate of motion is greater than the threshold, and therefore indicative of an unreliable estimate of motion, then the history variables are not updated and the estimated motion is replaced with values that vary predominantly with the history variables discussed above according to the following equations:

$$\Delta X = (3*history\_\Delta X + \Delta X)/4,$$

$$\Delta Z = (3*history\_\Delta Z + \Delta Z)/4,$$

$$\Delta \theta = (3*history\_\Delta \theta + \Delta \theta)/4.$$

Once again, the weights used in the weighted averages are only examples.

11. Frames being compared need not be consecutive. Instead of every frame being used, every Nth frame can be used (N=2,3 etc.).

12. Frames being registered need not be consecutive. Instead of every frame being used, every Mth frame can be used (M=2,3 etc.).

13. If every Nth frame is being used for motion estimation (N=2,3 etc.) then every Mth frame (M not necessarily equal N) can be used for registration or rendering.

14. The rendered image regions that are composited to form the extended field of view need not necessarily comprise the entirety of the respective image. Preferably only a subset of the image is composited, such as an image block extending over the full Z dimension and over a width in the X direction that is slightly wider than the search area. Preferably, the central region of the image is composited, since it generally has the best resolution.

15. The compositing method preferably includes the use of texture mapping, as found in the OpenGL Applications Programming Interface. See OpenGL Programming Guide (M. Woo et al.) published by Addison Wesley (1997). OpenGL is a trademark of Silicon Graphics.

16. A visible or acoustic warning is preferably given to the user in event of a poor motion estimate or a series of poor motion estimates, as described in U.S. Pat. No. 6,014,473. Such a warning can indicate to a user that a re-scan is required.

17. A user-visible icon (e.g. a variable length arrow) is preferably used to guide the user to make a scan at an optimal speed, as described in U.S. Pat. No. 6,014,473.

18. The registration method can be used in combination with ECG and/or respiratory triggering/gating. (Triggering is when acquisition is triggered by ECG or other events. Gating is when potential triggering events are analyzed to see if they are valid, i.e. they fit some predefined criteria.) For example, the selected images for registration alignment may be only those that are acquired in response to a selected trigger.

When forming the extended field of view of a pulsing object (e.g., an artery such as the carotid artery), it may be preferable to acquire only images during a particular portion of the cardiac cycle—such as end systole or some time interval after observed end systole. It is well known in ultrasound imaging to acquire an ECG signal using 3 ECG electrodes connected to the chest of the individual. The ECG signal exhibits some easily recognized peaks, such as the R wave. The R wave occurrence can be observed using an electronic trigger set to fire after each ECG voltage pulse surpassing some preset threshold is detected. This detected electronic trigger pulse can have a user-selectable delay applied to it and the resulting delayed electronic trigger used to trigger the start of an ultrasound image frame acquisition. Hence, ultrasound image frames are acquired once per heart cycle and at presetable delays from the detected R wave. It is also possible to use a gating technique wherein successive detected trigger pulses are compared with previously detected pulses and simple computer logic used to determine whether the ECG signal is gated or not. Typically, an ECG signal is gated only if the detected R wave interval falls within certain pre-programmed valid bounds. For example, suppose the R waves are occurring at 1000 mS intervals. A range of valid R waves can be set so that only R wave intervals in the range 900–1100 mS are gated. If one R wave signal is at 800 mS from the previous R wave, then it is associated with an irregular heart beat and ignored (since it may cause an image artifact due to irregular motion). This technique is discussed in McCann "Multidimensional Ultrasonic Imaging for Cardiology" Proc. IEEE Vol. 76, No. 9, September 1998, pp. 1063–1073.

19. During image composition, pixel values are preferably interpolated or averaged based on the pixel levels in the overlapping regions of the two registered frames, as described in U.S. patent application Ser. No. 08/916,585.

20. The images are preferably ultrasonic medical diagnostic images acquired with 1 D arrays employing a fixed focus in the elevation direction, one or more fixed foci in azimuth (transmit) and dynamic receive focus in azimuth. Ideally, a 1.5D array is employed that is focused in elevation, typically using a fixed transmit focus and a dynamically updated receive focus. Acuson Plano-Concave transducers as described in the related Hanafy U.S. Pat. No. 5,651,365, assigned to the assignee of this invention, can also be used.

Any suitable technology can be used for the transducer array, including piezoelectric ceramics (e.g. PZT), piezoelectric polymers (e.g. PVDF), relaxor ferroelectric ceramics (e.g. PMN-PT), and electrostatic transducers. Electrostatic transducers are described in "Micromachined Capacitive Transducer Arrays for Medical Ultrasound Imaging," X. C. Jin et al, Ultrasonic Symposium (Sendai, Japan, Oct. 5–8, 1988). The present inventors have recognized that such electrostatic transducers can be used in all conventional medical diagnostic ultrasonic imaging modes, including B-mode, Color Doppler mode, pulse wave mode, continuous wave mode, fundamental imaging mode, and harmonic imaging mode, with or without added contrast agent.

21. Registration and composition processing can be performed on-line (on the ultrasound system processor) or can be done off-line (at an arbitrary time after acquisition). If performed off-line, data compression such as JPEG compression can be used to speed data transfer.

22. The positioning of the search region for the test block can be varied adaptively: if the previous optimal value was found at 5 pixels to the right then the next search is preferably centered at 5 pixels to the right. Further details can be found in U.S. patent application Ser. No. 08/916,585.

For example, the current search can be centered on the offset estimated from the previous search. This is reasonable since the user typically uses a smooth motion in which a rapid change of velocity between successive frames is not expected. Suppose the first search is over the range +/−20 pixels. This is a 41 pixel search. However, if the optimum match (MSAD) is found at +10 pixels, then the subsequent search may be set to search from +5 pixels to +15 pixels (an 11 pixel search). In this way the search area is minimized and the overall speed improved. As well as changing the bias or center of the search, it is also preferred to vary the size of the search. If the successive searches are approximately uniform (e.g., 8, 7, 8, 9, 7 pixels all to the right), then it may be preferable to search the range +6 to +10. Alternately, if the successive searches are semi-random (e.g., 5, 7, 9, 3 pixels, all to the right), a better search range would be +1 to +15. Further, the size of the search can be made to vary according to the quality of the previous searches. If the ratio of MSAD (minimum SAD) to mean SAD is close to one, this means that the estimates are of poor quality, and that a high degree of uncertainty exists. In this case, larger search regions are preferred. Similar techniques can be applied to the rotational search.

23. The size of the test block can be varied adaptively. A small test block that yields good results is preferred because processing time is low. Otherwise, a bigger test block should be used to improve quality (e.g. the ratio of MSAD to mean SAD, or the similarity with respect to previous estimates). The decision to increase or decrease the test block size can be made on the basis of any quality measure, including those mentioned above.

24. Image resolution in the test block can be decimated (e.g. use only every Nth pixel in X and every Mth pixel in Z). The new pixel dimensions are then taken into account when determining motion in real units (mm). Preferably the image is low-pass filtered prior to decimation. Non-decimated images can be used for compositing even if decimated images are used for motion estimation.

25. The size of the image motion test block can be adaptively altered based on lack of signal at depth. If the lower (deeper) part of the test block is noisy (randomly varying levels—not like acoustic speckle which follows a pattern determined in part by the acoustic system point spread function) or if the deeper range part of the image is black, there is lack of good signal at greater depths, and the size of the test block can be reduced to ignore this region. For any given transducer and frequency there is a range (which can be experimentally measured) beyond which the displayed signal is unreliable because the acoustic signal is approximately the same size as or less than the electronic noise threshold of the system. This range can be pre-computed for all transducers and operating conditions or measured on test objects and then stored in a look up table. Whenever the system defines a test block to be used for motion estimation, it selects only pixels lying above (shallower) than the noise threshold region. An alternative method involves measuring acquired acoustic line data and detecting randomly varying signals. This can be performed using cross-correlation of successive signals, similar to the method used for Doppler detection of blood flow. If the lines are fired often enough, even if there is image motion the cross-correlation of signals will reveal a genuine detectable signal in the near field and no correlation in regions dominated by electronic noise.

26. If using harmonic data, the subject either may or may not contain non-linear scattering agent. Further the composited image may use a combination of fundamental and harmonic in the near field and fundamental only in the far field.

27. The rate of decorrelation can be used as an approximate estimate of transducer speed with respect to the imaged region and can be provided as a guide to the user. The rate of decorrelation can be derived using Doppler processors (correlators). Effectively, if a Doppler power signal is detected then there is motion. The size of this decorrelation signal is a function of speckle decorrelation.

Doppler cross-correlators can be used to correlate successive lines fired along one acoustic line direction. If the signal decorrelates by more than certain level (i.e., maximum cross-correlation level is below a threshold, e.g., 0.7), then this is an indication that the transducer has been moved too fast and the system displays a warning to the user. The advantage of this approach is that it allows the already-existing processing power of the ultrasound machine to be used to estimate whether the image acquisition is likely to be effective before the image acquisition is complete and the potentially time-consuming image transfer process has begun.

The rate of motion can be estimated using the Color Doppler processors already present in most ultrasound machines. This allows an indication to the user of poor speed control (i.e. transducer movement that is fast or out of plane) before the motion estimation process. In some cases, it is easier to do the motion estimation after complete image sequence collection and hence there is value in having an approximate estimate or warning of possibly non-optimal acquisition.

Effectively, the Doppler processors are used to measure pulse to pulse decorrelation. In one embodiment, beamformed I,Q signals are applied to the B-mode processor and to the Color Doppler processor. Generally, different acquisitions are used for the B-mode and Color Doppler signals (Doppler signals are typically more narrowband). Once the baseband, beamformed signals are filtered, Doppler processing is performed on the I and Q signals to derive Doppler-related frequency estimates resulting from motion. Doppler processing is well known in the art. See for example "Real time two dimensional blood flow imaging using an autocorrelation technique," Kasai et al. Tran. Sonics and Ultrasonics, Volume SU-32, pages 458–464 (1985). See also the detailed discussion in Maslak, U.S. Pat. No. 5,555,534, assigned to the assignee of this invention.

The Color Doppler processor typically includes low-pass filters, clutter filters and an autocorrelator. The clutter filters are typically formed as delay line cancellers, and they are used as low frequency rejection filters to eliminate large echo signals from stationary and slow moving objects which have low or zero Doppler frequency shift. The autocorrelator autocorrelates signals from the clutter filters and produces output signals for a Doppler Energy calculator, a Doppler Variance calculator and a Doppler Velocity calculator.

In the current application, the Doppler Energy signal is of greatest interest. Generally, a significant Doppler Energy signal may be associated with too rapid motion of the transducer relative to the region being imaged and used to generate a warning to the user. Similarly, a sudden motion will cause a color flash to appear. Color flash is well known in diagnostic ultrasound. Essentially, it is this flash indication which is being used here to highlight a sub-optimal motion. Since the application does not specifically require a determination of Doppler Energy over a 2D region (except when forming an extended view image of Doppler Energy images), a very narrow examination of the image may be made to determine if there is excessive Doppler Energy present. Typically one scans numerous acoustic lines to map out a 2D region. However, for the current application it is sufficient to fire Doppler associated acoustic lines in a single direction interleaved with the B-mode beams used to acquire the B-mode parent image. Ideally, these lines are oriented at a non-zero angle with respect to the normal to the transducer face. This improves the Doppler angle for azimuthal motion. (Doppler processors detect the component of motion parallel to the beam and hence it is preferable to orient the beam so that it has at least some component in the azimuthal direction.) By experimentation, one determines the correct setting for the clutter filter to remove near DC components, and the Doppler Energy threshold above which the machine produces an indication that transducer velocity may be excessive. Typically, to minimize noise one can integrate the Doppler Energy signals derived over time as the Doppler processor determines the Doppler Energy level for increasing range associated with a Doppler line firing. (Conventionally, the Doppler Energy levels are compared to a threshold as they are acquired and if they exceed a threshold a colored pixel is drawn corresponding to the associated position in range and azimuth on the B-mode image.) When Doppler Energy is used for determining sub-optimal motion, one can tailor the clutter filter setting and the energy threshold above which one assumes that non-optimal motion has occurred.

Experiments with different transducers and different frequencies can be performed to determine the relationship between speckle decorrelation (between two line firings at a known time interval along the same line axis) and speed of motion in the elevation direction. Experiments can also be performed to determine the optimal transducer speed (or maximum and maximum workable speeds) and these can be compared with the decorrelation values for different speeds. These values are preferably stored in a look up table in the system. During operation, the system takes account of transducer type and frequency and estimates speed of transducer motion from the measured line-to-line decorrelation value. If this speed is too high or too low, an indication is graphically displayed on the system screen. Alternatively, the estimated speed is displayed.

The output of the evaluation of the Doppler Energy determination can be presented to the user in a number of ways.

(a) A binary indicator can be displayed advising the user when sub-optimal transducer motion has been detected.

(b) A numerical output indicating relative Doppler Energy level can be displayed—either the maximum value for a particular frame to frame case or the mean Doppler Energy level over the entire scan.

(c) A Color Doppler Energy representation can be displayed on the screen in the conventional manner. In this case, a line-like Color Energy region appears on the image, and the user simply observes whether it flashes.

In addition to using the Doppler power or energy signal to detect poor motion estimates by means of the flash signal, it is also possible to use the Doppler velocity estimators to estimate transducer motion. Preferably, a Doppler velocity acquisition line is oriented at a non-zero angle with respect to a line oriented perpendicular to the transducer face (e.g. 45 degrees). When a velocity of for example 10 mm/s is detected, one can infer the scanning velocity in the pure azimuthal direction since we can assume that the actual transducer motion is parallel to the azimuthal direction. The velocity estimated for the transducer motion after correction for the Doppler angle (45 degrees) is 10/cos(45 degrees)=14.1 mm/s. This value can be output to the display numerically or graphically. Alternatively, the detected azimuthal velocity is compared to a threshold velocity (above which image alignment processing becomes problematic), and a warning is presented to the user by visual or audible means.

Similarly, the PW or CW Spectral Doppler processor can be used to estimate the velocity of the transducer probe relative to the tissue being imaged (the "sweep velocity"). The velocity is derived from the frequency component occurring with highest signal level from among the various frequency components examined.

In all cases, the Doppler parameters such as filter settings, pulse shapes and threshold levels are preferably optimized by modeling or experimental techniques as is well known in the art.

Figure 10:
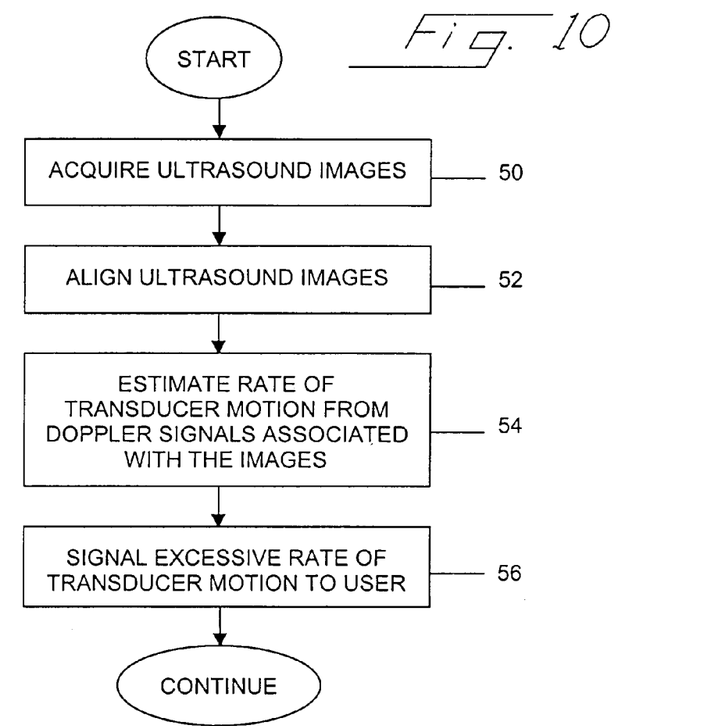
FIG. 10 is a flow chart of another preferred embodiment of the method of this invention.

FIG. 10 provides an example of a method for using Doppler signals to estimate the rate of transducer motion in an image alignment method. As shown in FIG. 10, the first steps 50, 52 are to acquire multiple ultrasound images and to align the ultrasound images. Preferably, this alignment is performed as discussed above. However, for this aspect of the invention it should be understood that any suitable alignment method can be used, including those described in co-pending U.S. patent application Ser. No. 08/916,585 and in Weng U.S. Pat. No. 5,575,286.

The rate of transducer motion is estimated in step 54 from Doppler signals associated with the images. This motion estimate can be made as described above, and the motion estimate is then used in step 56 to signal an excessive rate of transducer motion to the user. As pointed out above, this can be done by a visual or an audible alarm, or by indicating the actual estimate of transducer motion to the user visually.

28. Pixel values can be interpolated between acquired values to yield a higher accuracy motion estimate (effectively giving sub-original pixel resolution). This interpolation process is well known and is often performed by the scan-converter. The interpolation may be linear (either in X or Y or both) or it may be curve-based. For example, a cubic spline can be fit to available data. Linear interpolation is usually adequate and is often faster. In practice sub-pixel estimation using the quadratic fit technique described above is often more efficient.

29. When multiple, partially overlapping frames are combined after registration as described above, the combination can be performed in many ways. For example, pixel I (i, j) of the combined image can be formed as a simple average:

$$I_{(i,j)} = (I_{(i,j)}^{Frame1} + I_{(i,j)}^{Frame2} + I_{(i,j)}^{Frame3})/3.$$

Alternately, non-uniform weights can be used, e.g. [0.25, 0.5, 0.25]. Also, recursive compounding techniques can be used:

$$I'_{(i,j)} = \alpha(I_{(i,j)}^{FrameN}) + (1-\alpha)I_{(i,j)},$$

where IFrameN is a newly acquired frame of data, I(i, j) is the currently existing pixel data, and I'(i, j) is the modified pixel data that takes into account the existing pixel data, the newly acquired data, and α. In general, α is less than one and may be equal to 0.3, for example. (If I(i, j) has not been created, then α=1). With this approach, each compounded frame overwrites or modifies the previously-compounded pixel values from earlier frames based on the new pixel values. The compounded image can then be optimized using histogram equalization to improve contrast or using the method described in Ustuner U.S. Pat. No. 5,479,926, assigned to the assignee of the present invention.

Figure 13:
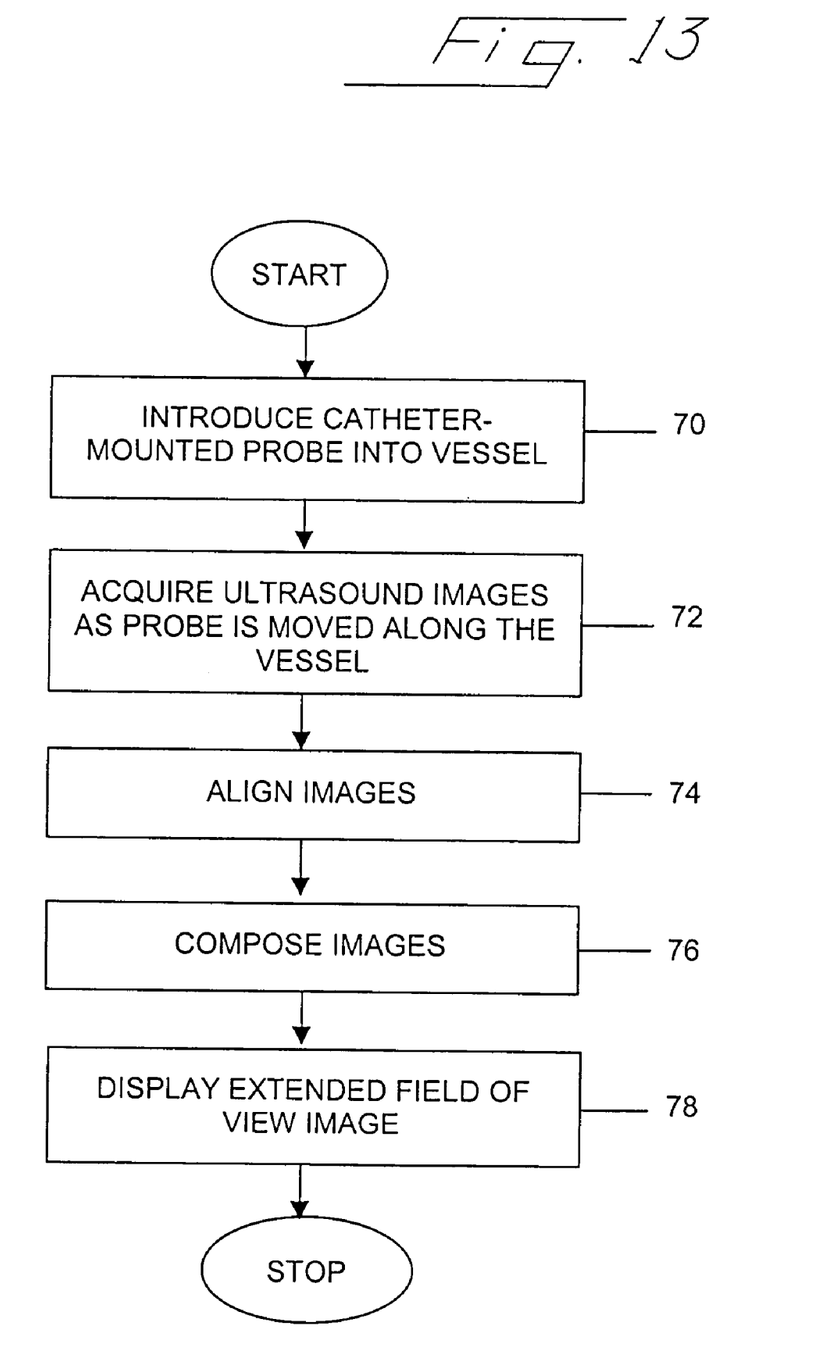
FIG. 13 is a flow chart of another preferred embodiment of the method of this invention.

30. FIG. 13 provides a flow chart of an imaging method that utilizes the image acquisition, alignment, and composition techniques described above to create an extended longitudinal section of a tubular organ such as a blood vessel. In step 70 a catheter-mounted probe is introduced into a tubular organ such as a vessel, typically by inserting the probe into a lumen of the vessel. For example, the probe can include an ultrasonic transducer array mounted on a catheter for insertion into a human vein or artery. In step 72 ultrasound images are acquired as the probe is moved along the vessel, either into or out of the body of the subject. In step 72 the images are acquired in respective image planes that are oriented generally parallel to the path along which the probe is moved. In step 74 the images acquired in step 72 are aligned, using an of the alignment techniques now known or later developed by those skilled in the art. In step 76 the aligned images are composited, and in step 78 the extended field of view image as composited in step 76 is displayed. The composited image of step 76 is in this example an extended longitudinal sectional view of the vessel.

The techniques described above allow for viewing of long sections of vessels and surrounding anatomy and also allow for viewing landmark tissue to allow the user to orient a region of interest, which may be a small area in many situations, in a context of a larger image including such landmark tissue. Examples of suitable catheter-mounted transducer probes are described in U.S. patent application Ser. Nos. 08/791,598 and 08/802,621, both assigned to the assignee of the present invention and incorporated by reference herein.

31. When an extended view image is being acquired using a low frame rate and a relatively high manual transducer sweep rate across the tissue surface, a dimensional error is encountered. This is because the ultrasound system typically scans the array from one side to the other side of the transducer array. If the transducer array is 50 mm wide, the frame rate is 10 frames per second, and the transducer is scanned at a rate of 5 mm/s, then in the time it takes to scan one frame (0.1 s) the transducer has moved 0.5 mm. When the transducer array is scanned in one direction this error corresponds to a 0.5 mm image extension and when scanned in the other direction it corresponds to a 0.5 mm image contraction in the azimuthal motion. (This is a 1% dimensional error.) This error scales with scan rate and inversely with frame rate. During extended field imaging, we can determine the image motion and hence it is possible to correct for this effect.

Consider the case where the system scans from transducer element #1 (at one end of the array) to transducer element #N (at the other end of the array). If the motion estimator detects a motion between two frames of 1 mm in the direction of element 1, then the real image region which has been scanned has contracted by 1 mm. Hence we must scale the width of the region by a scale factor K, where $K$=1−(1 mm/Image width(mm)), $K$=1−1/50=0.98 for a 50 mm wide image.

Similarly, for motion in the other direction, the scale factor K is set equal to 1+1/50 to extend the width of the imaged region. The motion estimate (translation) is preferably corrected by the same factor, i.e. the estimated translation is multiplied by 0.98 in the above example for transducer motion in the direction of element #1. See the discussion of image correction in U.S. patent application Ser. No. 08/916,358, assigned to the assignee of the present invention and hereby incorporated by reference herein.

The motion of the probe also affects the determination of rotation, and estimates of rotation should also be modified. Typically, the angular estimate is derived from the angle associated with the relative motion of pixels in the azimuthal direction at the top and bottom of the search block. This angle must now be corrected to take account of the fact that the X dimensions of the pixels are different from that originally assumed. For the small angles of interest here, this can be effected approximately by multiplying the angles produced before trying to determine the transducer probe velocity error by the factor determined above for the correction to the image azimuthal dimension and motion estimate, i.e. the estimated rotation is multiplied by 0.98 in the example above for transducer motion toward transducer element #1.

The simplest way to implement this correction is to modify the texture mapping width when doing the image compositing using OpenGL texture mapping.

32. When compositing an image including Color Doppler data (velocity or energy), it is preferable to acquire separate B-mode and Color regions as is conventionally done inside the system. Typically, an ultrasound machine acquires a complete frame of B-mode and a partial frame of Color. Depending on the level of Color Energy and/or Velocity, particular pixels are overwritten or mixed with color values. Color regions do not in themselves contain the speckle data used in motion estimation of the type described above. Therefore, it is preferable to use the raw B-mode images for motion estimation prior to the Color superimposing step.

On occasion, only the color superimposed images are available for estimating transducer motion. There are a number of methods that can be used, as follows:

(a) The Color pan boxes can be restricted in size to a small part of the parent image. The color pixel data, which contains no speckle motion data, does not corrupt the motion estimate to any significant extent.

(b) A color superimposing step can be used which mixes Doppler Color and B-mode speckle. Thereafter, the B-mode speckle is processed by referring to the Color lookup table and inferring the underlying B-mode value. If necessary, the B-mode values are rescaled if they were scaled during the color mapping process.

(c) The Doppler Color regions can be restricted to specified regions of the parent image. Typically only a portion of the parent image is Doppler processed since Doppler processing is associated with slow data acquisition and associated slow frame rates. Preferably, the Color pan box is limited to only a portion of the available image, and preferably the Color pan box is prohibited from the center of the test block which is being used for motion estimation. Although this may sound unduly burdensome, it is not necessary that the majority of the image be in color since only small portions of the image are used in composition to form an extended field of view. If these small regions are color regions, then an extended color image will still result. This assumes that the composited regions are different from the region used for motion estimation. In this process, motion is estimated for the B-mode region. One then takes account of the difference between the center of the motion estimation block and the center of the color composited region during image composition. The simplest way to do this is to define the composited region to include the center of the motion estimation region but to define that the portion of the image composition region outside that containing color as completely transparent. OpenGL™ texture mapping allows for controlled transparency and hence this technique is easily implemented.

(d) The Color pan box region alternately can be allowed to occur anywhere in the frame as long as it does not occupy the entire frame. Prior to motion estimation, the program uses knowledge of the location of the color regions (which may be passed to it from the image acquisition controller of the ultrasound machine), and adaptively alters the position of the motion estimation block to position it on one or other side of the Color region. In this way, the region for the motion estimation process is spaced from the Doppler Color region of the parent image. Moving the Color box during acquisition can be prohibited, and to simplify implementation, this adaptive step is performed only at the beginning of the process.

Figure 11:
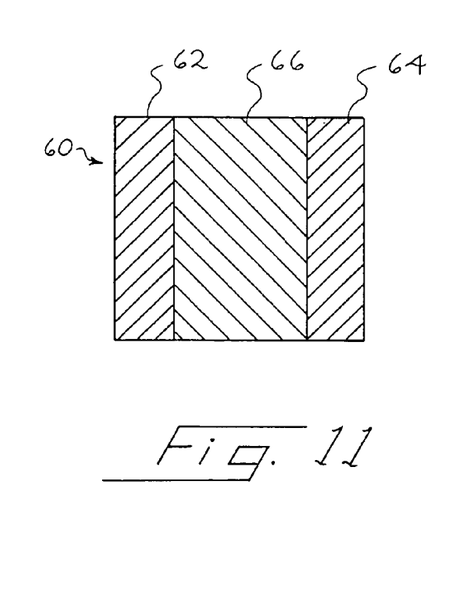
FIGS. 11 and 12 are diagrammatic views showing the spatial relationship of B-mode and color Doppler regions in a parent image.
Figure 12:
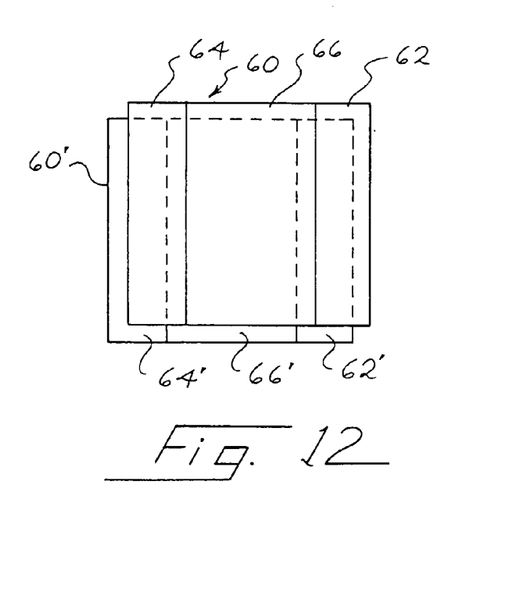

FIG. 11 shows one preferred relative arrangement of regions within a parent image. In this case, the parent image 60 includes two B-mode regions 62, 64 and a Color Doppler region 66. The B-mode regions 62, 64 are well suited for motion estimation using any of the techniques described above, and the relative positions of the B-mode regions 62, 64 and the color region 66 are well known. As shown in FIG. 12, when two parent images 60, 60' of the type shown in FIG. 11 are composited, the B-mode regions 62, 62' can be used for motion estimation and alignment of the two parent images 60, 60', while the color regions 66, 66' can be used for extending the field of view.

33. Typically, the test block is smaller than the entire parent image, but it is also possible to use the entire image as the test block. In this case, it is preferred to account for the fact that there is incomplete matching data for any non-zero motion (i.e. if the frames move from left to right, then one frame will lack data for comparison on the left hand side and the other will lack data on the right hand side). In the MSAD calculation (or cross correlation), it is important that valid data be present. Therefore, when using a full frame test block, one preferably suppresses SAD calculations for invalid regions. However, in order to calculate the minimum SAD, one preferably uses some form of normalization to take account of the fact that some comparisons use more pixels (since they are less overlapping). One approach is to replace the search for minimum SAD with a search for minimum normalized SAD, where the normalized SAD operation normalizes the SAD by dividing the SAD by the number of pixel-to-pixel comparisons being used.

As an example, consider a full image block of 100 by 100 pixels, where the search is ±3 pixels (left and right).

When calculating the SAD with a shift of three pixels to left, the three pixels on the left are invalid (not defined) on one frame, and three pixels on the right are invalid (not defined) on other frame. Therefore, the number of comparisons is (100−3−3)*100=9400. In this case, the normalized SAD is equal to the SAD divided by 9400.

When calculating the SAD with a zero pixel shift between the test blocks, no pixels on the left are invalid (not defined) on one frame and no pixels on the right are invalid (not defined) on the other frame. Therefore, the number of comparisons is (100−0−0)*100=10,000. In this case, the normalized SAD is equal to SAD divided by 10,000. Of course, a full-frame test block may be sub-sampled as described above, e.g. decimated.

34. If image acquisition is not ECG gated (as is most often the case), then it is preferable to take steps to minimize perceived pulsatility in the resulting color Doppler extended field of view image. (Pulsatility will appear as a color region with rapidly changing width as a function of azimuthal position and the respective component image). One approach is to persist the Color Doppler data by separating it from the underlying B-mode and then persisting it during the compositing step. If the Color Doppler data is not available independently from the B-mode data from the ultrasound image processor, then the Color data can be separated from the combined Color+Gray scale (B-mode) data by detecting regions in the images in which R, G and B are not balanced (RGB balanced=gray). These regions (identified as Color) are then persisted such that the maximum Color value detected for any overlapping region during composition overwrites any previous Color value or the Gray value if no Color value already exists at that point. Alternatively, the Color data is separated into a separate Color image zone comprising Color values and a high opacity (possibly opacity=1), and non Color values (everywhere else) with opacity=0. During OpenGL texture mapping, the Color regions will overwrite such that the peak flow condition for any particular region will dominate and perceived pulsatility is suppressed. When using this technique, it is preferable that the Color map used is continuous and exhibits a monotonic type variation for increasing Color Doppler Energy or Color Doppler Unsigned Velocity. (If signed velocity is used then dramatically changing colors corresponding to changes in flow direction may result in an undesirable image with blotches of different color.)

CONCLUSION

The improvements and modifications described in sections 1–34 above can be used with any suitable algorithm for registering two or more substantially coplanar ultrasound images. The embodiments described above may be implemented on an ultrasound imaging system or on an offline processor. Once an extended field of view image has been formed as described above, it can be manipulated in well known ways, as for example by zooming or rotating using OpenGL. All of the techniques described herein may be used with tracking image frames of the type discussed in U.S. patent application Ser. No. 08/916,585. The foregoing detailed description has described only a few of the many forms that this invention can take. For this reason, this detailed description is intended by way of illustration and not by way of limitation. It is the following claims, including all equivalents, that are intended to define the scope of this invention.

What is claimed is:

1. A medical ultrasound diagnostic image registration information determination method comprising the following steps:
   (a) selecting first and second medical ultrasonic diagnostic images acquired with a transducer probe;
   (b) finding a translation between the first and second images that provides an improved match therebetween; then
   (c) finding a rotation between the first and second images that provides an improved match therebetween with the first image aligned relative to the second image based on the translation determined in step (b); and
   displaying a third image as a function of the rotation.

2. The method of claim 1 further comprising the following steps:
   (d) finding an additional translation that improves the match between the first and second images, given the translation determined in step (b) and the rotation determined in step (c); and
   (e) finding an additional rotation that improves the match between the first and second images, given the translations determined in steps (b) and (d) and the rotation determined in step (c).

3. The method of claim 1 wherein the images selected in step (a) are characterized by a ratio of widest range extent/widest azimuth extent that is greater than 5.

4. The method of claim 1 wherein the images selected in step (a) are characterized by a ratio of widest range extent/widest azimuth extent that is greater than 9.

5. The method of claim 1 wherein the images selected in step (a) are complexity-reduced versions of respective more complex parent images.

6. The method of claim 5 wherein the images selected in step (a) are reduced in complexity with respect to the respective more complex parent images in at least one of area, pixel density and pixel contrast resolution.

7. The method of claim 6 wherein step (a) comprises the step of adaptively selecting the size of test images used in steps (b) and (c).

8. The method of claim 6 wherein step (a) comprises the step of sizing a test block to eliminate from the test block at least one region of the respective parent image characterized by lack of signal.

9. The method of claim 1 wherein the images selected in step (a) are modified versions of respective parent images in at least one of area, pixel density, contrast resolution, contra brightness, and spatial frequency spectrum.

10. The method of claim 1 wherein the images comprise color Doppler information.

11. The method of claim 1 wherein the images comprise at least one of fundamental and harmonic image information.

12. The method of claim 1 wherein the translation of step (b) is found to sub-pixel resolution.

13. The method of claim 1 wherein the rotation of step (c) is found to sub-angular-step-size resolution.

14. The method of claim 1 wherein the first and second images are selected in response to at least one of ECG gating, ECG triggering, respiratory gating and respiratory triggering.

15. The method of claim 1 further comprising the step of:
   (d) assessing speckle decorrelation between the images.

16. The method of claim 15 further comprising the step of:
   (e) providing an indication to a user based on the speckle decorrelation assessed in step (d).

17. The method of claim 1 further comprising the step of:
   (d) compositing at least a portion of the first and second images by combining image values in an overlapping region of the first and second images.

18. The method of claim 1 further comprising the following step:
   (d) finding an additional translation that improves the match between the first and second images, given the translation determined in step (b) and the rotation determined in step (c).

19. The method of claim 1 further comprising the following step:
   (d) finding an additional rotation that improves the match between the first and second images, given the translation determined in step (b).

20. The method of claim 1 wherein step (b) comprises the step of finding the translation that best matches the images.

21. The method of claim 1 wherein step (c) comprises the step of finding the rotation that best matches the images.

22. A medical diagnostic ultrasound imaging method comprising the following steps:
   (a) introducing a catheter-mounted intra-cavity ultrasonic transducer probe into a lumen of a subject;
   (b) acquiring a plurality of ultrasonic images from the probe as the probe is moved along a pad within the subject, the plurality of ultrasonic images being co-planar;
   (c) aligning a plurality of the images; and
   (d) compositing the aligned images.

23. The method of claim 22 wherein the lumen is formed by a vessel, and wherein step (b) comprises the step of acquiring the images in respective image planes oriented generally parallel to the path.

24. The method of claim 22 wherein step (d) comprises the step of compositing the aligned images to form an extended longitudinal sectional view of the vessel.

25. A medical diagnostic ultrasound imaging method comprising the following steps:
   (a) acquiring, with a transducer probe at different positions, first and second medical ultrasonic diagnostic images;
   (b) finding, with a processor, an alignment that improves the match between the first and second images; and (c) estimating a rate of transducer motion of the transducer probe, the estimating being from Doppler signals associated with the first and second images.

26. The method of claim 25 wherein step (c) comprises the step of estimating the rate of motion from Doppler energy signals associated with the first and second images.

27. The method of claim 25 further comprising the step of
(d) presenting to a user a signal indicative of the rate of motion.

28. The method of claim 25 further comprising the step of
(d) presenting to a user an alarm indicative of excessive motion between the images.

29. The method of claim 25 wherein the Doppler signals and each of the images are included in non-overlapping portions of respective parent images.

30. The method of claim 25 further comprising the step of
(d) acquiring the Doppler signals by interleaving Doppler signal acquisition with first and second image acquisition.

31. The method of claim 25 further comprising the step of
(d) correcting the alignment determined in step (b) based on the rate of transducer motion determined in step (c).

* * * * *